United States Patent [19]

Beebe et al.

[11] Patent Number: 5,592,402
[45] Date of Patent: Jan. 7, 1997

[54] METHOD FOR INTERPRETING COMPLEX DATA AND DETECTING ABNORMAL INSTRUMENT OR PROCESS BEHAVIOR

[75] Inventors: Kenneth R. Beebe; Glen H. Hughes; Harry D. Ruhl; Richard C. Winterton, all of Midland, Mich.

[73] Assignee: The Dow Chemical Company, Midland, Mich.

[21] Appl. No.: 430,093

[22] Filed: Apr. 26, 1995

Related U.S. Application Data

[63] Continuation of Ser. No. 200,804, Feb. 18, 1994, abandoned, which is a continuation of Ser. No. 869,607, Apr. 16, 1992, abandoned.

[51] Int. Cl.$^6$ .............................. G06G 7/48; G06G 7/58; G01N 31/00
[52] U.S. Cl. .................. 364/578; 364/497; 364/498; 73/23.23; 73/23.35
[58] Field of Search ......................... 364/571.01, 571.05, 364/572, 578, 577, 576, 571.02, 571.04, 554, 485, 496, 497, 413.01, 507, 509, 510, 550, 431.11, 499, 569; 73/23.23, 23.35, 29.02, 577, 599, 61.52

[56] References Cited

U.S. PATENT DOCUMENTS

| | | | |
|---|---|---|---|
| 4,338,811 | 7/1982 | Miyagi et al. | 73/23.1 |
| 4,546,643 | 10/1985 | Bonneyrat et al. | 73/61.1 |
| 4,631,687 | 12/1986 | Kowalski et al. | 364/497 |
| 4,674,323 | 6/1987 | Rulf et al. | 73/61.1 |
| 4,802,102 | 1/1989 | Lacey | 364/497 |
| 4,807,148 | 2/1989 | Lacey | 364/498 |
| 4,835,707 | 5/1989 | Amano et al. | 364/497 |
| 4,835,708 | 5/1989 | Frans | 364/498 |
| 4,837,726 | 6/1989 | Hunkapiller | 364/498 |
| 4,893,253 | 1/1990 | Lodder | 364/497 |
| 4,916,645 | 4/1990 | Wuest et al. | 364/571.04 |
| 4,941,101 | 7/1990 | Crilly | 364/497 |
| 4,944,921 | 7/1990 | Colby et al. | 422/70 |
| 5,025,389 | 6/1991 | Imai | 364/497 |
| 5,121,337 | 6/1992 | Brown | 364/571.01 |
| 5,121,443 | 6/1992 | Tomlinson | 382/89 |
| 5,210,778 | 5/1993 | Massart | 378/53 |

OTHER PUBLICATIONS

Puchwein et al., "Outlier Detection in Routine Analysis of Agricultural Grain Products By Near-Infrared Spectrometry", *Analytica Chimica Acta*, 223 (1989) 95–103 Jan. 1989.

*Primary Examiner*—Kevin J. Teska
*Assistant Examiner*—Jacques H. Louis-Jacques
*Attorney, Agent, or Firm*—James T. Hoppe

[57] ABSTRACT

An improved method is provided for determining when a set of multivariate data (such as a chromatogram or a spectrum) is an outlier. The method involves using a procedure such as Principal Component Analysis to create a model describing a calibration set of spectra or chromatograms which is known to be normal, and to create residuals describing the portion of a particular spectrum or chromatogram which is not described by the model. The improvement comprises using an average residual spectrum calculated for the calibration set, rather than the origin of the model as a reference point for comparing a spectrum or chromatogram obtained from an unknown sample. The present invention also includes separating a complex set of data into various sub-parts such as sub-chromatograms or sub-spectra, so that outliers in any sub-part can be more readily detected. In one particular embodiment, the invention is directed towards a method for dividing a chromatogram into the sub-parts of peak information, baseline shape, baseline offset, and noise.

26 Claims, 4 Drawing Sheets

METHOD FOR INTERPRETING COMPLEX DATA AND DETECTING ABNORMAL INSTRUMENT OR PROCESS BEHAVIOR

CROSS-REFERENCE TO RELATED APPLICATION

This is a continuation of application Ser. No. 08/200,804, filed Feb. 18, 1994, which is a continuation of application Ser. No. 07/869,607 filed Apr. 16, 1992, both now abandoned.

BACKGROUND OF THE INVENTION

1. Field of the Invention

This invention relates to a method of analyzing multivariate data generated by an instrument in order to determine whether abnormal features are present. More particularly, this invention relates to an improved method for rapidly identifying instrumentation or process failures in a chemical system.

2. Description of the Prior Art

On-line analytical instrumentation generates data that is used in a wide variety of applications, such as closed-loop control of a process, quality assurance of a product, or environmental and safety functions. Often, this data is in the form of multivariate data such as absorbance readings at various wavelengths, a detector response at various times, or any other set of data that consists of multiple measured values on each individual sample. The reliability of the data depends largely upon the performance of the instrument used to generate the data. If the instrument fails to work properly, the data generated may contain little if any valid information.

Problems with analytical instruments are often first detected when an individual notices that unusual data is being generated. Unexpected peaks, larger than expected noise levels, and baseline offsets are just a few of the features that may lead the individual to question the validity of a chromatogram or spectrum. Monitoring the data as it is generated for the appearance of these unusual features allows for the detection of developing problems before they become severe enough to affect the ongoing analysis. Individuals monitoring the raw chromatogram or spectrum data perform the largely unconscious activity of learning from experience what a "normal" set of data looks like and then deciding whether the present set of data is reasonably similar. Unfortunately, it is not practical to manually monitor all of the data, as many on-line instruments produce more than a thousand sets of data per day.

Repetitive manual tasks, such as monitoring large amounts of produced data, are generally capable of being automated through the use of computers. Furthermore, computers are widely used to collect the data generated by on-line instruments, and so are readily available to perform routine monitoring. Unlike an analyst, however, computers cannot perform any "unconscious" activity. Accordingly, in order to monitor the data for abnormal features, the computer must first be programmed to identify normal features in a spectrum or chromatogram.

The field of study that deals with teaching the computer to emulate the process of learning and recognizing features in data is called pattern recognition. Pattern recognition techniques are typically used to sort sets of data into groups having similar features. In outlier identification, however, only one group is identified which is defined by the features in a set of data containing only sets of multivariate data which are known to be normal.

Outlier identification is accomplished by first teaching the computer to recognize "normal", "acceptable" or "expected" features in multivariate data known to be normal. When a new spectrum or chromatogram is obtained, its features are compared to what is expected. If the data has additional features, or lacks significant features, it is labelled "abnormal", "unacceptable", or an "outlier". Outliers may be the result of many different causes such as instrument failures, mechanical problems or process problems such as impurities in the analyzed materials. Pattern recognition techniques are able to identify any changes in the appearance of the data, regardless of its source, whereas simpler systems which are programmed to signal the operator whenever certain unwanted values are reached, can only be used to detect foreseen problems. Accordingly, when pattern recognition techniques are used, the potential for abnormalities in the data being undetected is reduced.

Principal Component Analysis (PCA) is one procedure that can be used as a pattern recognition technique. PCA will be used below to illustrate the invention, but it should be understood that the present invention can be used with any technique which can model features in the data (e.g. Partial Least Squares technique—see P. Geladi, and B. R. Kowalski, *Analytica Chemica Acta*, 185, pg. 1, 1986).

One way of describing how PCA works is to think of PCA reorienting a set of data so that each spectrum or chromatogram becomes a single point in a multidimensional space. The number of measurements which make up the original spectrum or chromatogram defines the number of dimensions in the new coordinate system. A group of calibration chromatograms or spectra which the analyst has determined to be representative of the expected spectra or chromatograms can be placed in this coordinate system forming a cloud of points in the multidimensional space. PCA mathematically describes this cloud of points using as few dimensions (or principal components) as possible. Residual sets of multivariate data (residuals) which identify the portion of each calibration spectrum or chromatogram which was not contained within the model are then calculated. The sum of the squares (SS) of the residuals are then compared with the SS of the residuals obtained for unknown samples to see if the unknown samples are within the proper range.

The current uses of the PCA method for outlier detection are only concerned with the SS of the residual spectra (see Gerd Puchwein and Anton Eibelhuber, "Outlier Detection in Routine Analysis of Agricultural Grain Products by Near-Infrared Spectroscopy", *Analytica Chemica Acta*, 223, pp. 95–103, 1989). This is analogous to using the square of the Euclidean distance of the residual spectrum from the origin. Theoretically, the PCA model could be constructed to take into account all features of the calibration set. This would result in residual spectra randomly distributed about the origin as the residual spectra would only contain random noise. In this situation the SS of the residual spectra is an appropriate measure of normality. Experience has shown, however, that when more principal components are added to the model in order to describe every feature in the calibration chromatograms or spectra, the model becomes too close a fit of the calibration set data; the model begins to fit the noise in the data (overfitting). When this happens, the unknown samples which should be classified as normal will be classified as outliers because their noise structure will not be identical to the noise structure of the members of the calibration set. Therefore, a better approach would be to use fewer principal components in the modeling, and allow relatively small features to remain in the residual spectra. In this situation the residual spectra are not distributed about the origin, and therefore, the SS of the residual spectra is no longer an appropriate measure of the acceptableness of the spectra. To take into account the location of the residual spectra relative to the origin, the average of the residual spectra is used as a reference point rather than the origin. Consequently, this approach avoids overfitting by reducing the number of principal components and increases the sensitivity for detecting abnormal features or outliers by using the average residual spectrum as a reference point.

Furthermore, the PCA method cited above has been applied only to near infrared spectra. Further difficulties are encountered when expanding the known pattern recognition techniques to chromatographic applications. In chromatographic applications, some features of the data are expected to change over time. For example in gas chromatography, as the column ages, changes in the baseline become more prevalent. If the baseline offset or shape changes, all of the data being produced will be labelled outliers, even though valid peak data is being generated.

OBJECTS OF THE INVENTION

It is an object of the present invention to provide a method which is more sensitive than known methods for determining when a spectrum is an outlier.

Another object of this invention is to provide a sensitive method for determining outliers which can be used for any form of multivariate data.

Still another object of this invention is to provide a method for separating a set of multivariate data into various sub-parts, so that each sub-part may be evaluated separately, thereby increasing the sensitivity of an analysis such as outlier detection.

SUMMARY OF THE INVENTION

The present invention is directed to an improved method for detecting outliers in a system which collects sets of multivariate data such as chromatograms or spectra. The method involves using a procedure such as Principal Component Analysis to create a model describing a calibration set of spectra or chromatograms which is known to be normal, and to create residuals describing the portion of a particular spectrum or chromatogram which is not described by the model. The improvement comprises using an average residual calculated for the calibration set, rather than the origin of the model as a reference point for comparing a spectrum or chromatogram obtained from an unknown sample. This improvement allows increased sensitivity towards detecting outliers.

The present invention is also directed to separating a complex set of data into various sub-parts such as sub-chromatograms or sub-spectra. In one particular embodiment, the invention is directed towards a method for dividing a chromatogram into the sub-parts of peak information, baseline shape, baseline offset, and noise. Dividing a set of multivariate data in this way allows the detection of outliers to be more sensitive to changes in one or more of the sub-parts.

The invention is also directed towards an improved method for carrying out an automated chemical reaction. The method incorporates the method for detecting outliers as a way of checking for changes in the feedstock, chemical process and instruments. If any of these items fails, multivariate data produced in the course of the process will reflect the failure. The current invention allows these changes to be automatically detected as soon as they occur.

Additional advantages and features of the present invention will become apparent from a reading of the detailed description of the preferred embodiment which makes reference to the following set of drawings in which:

DESCRIPTION OF THE PREFERRED EMBODIMENTS

It should be understood that the method of this invention can be applied to any set of multivariate data capable of being measured such as chromatograms or spectra. For purposes of this discussion, however, it will be assumed that the data being analyzed is a spectrum consisting of absorbance data at various wavelengths.

According to the method of the invention, the first step is collecting a set of representative multivariate data. This set of data will be used to teach the computer what features are contained in "normal" spectra or chromatograms. Therefore, the spectra should be manually selected to ensure that they are representative of the type of spectra expected to be obtained.

Once a calibration set of data has been chosen, a procedure such as principal component analysis (PCA) is used to construct a model describing the data. The following discussion is meant to help visualize how PCA operates. Traditionally, a spectrum consisting of absorbance readings at a large number (e.g. 300) of wavelengths is represented as a function wherein the ordinate is the level of absorbance while the abscissa is divided up into wavelengths. Thus, for every wavelength there is an absorbance point. In PCA each spectrum or chromatogram can be thought of as being represented as a single point in a multidimensional axes system. A spectrum consisting of data at 300 wavelengths, for example, would be represented as a single point in a 300 dimensional space. Accordingly, the number of dimensions needed is equal to the number of absorbance data points in the traditional system.

Each member of the calibration set is plotted in the same multidimensional space, creating a cloud of points, each point representing one spectrum. The more similar the original spectra were, the tighter the cloud will be. This cloud can be exactly described using at most r principal components, where r is determined by the lesser of the number of dimensions in the multidimensional space, and the number of points making up the cloud. Much of the variability of the cloud can be described using many fewer principal components, as the original spectra are largely similar. PCA is used to create a model describing the cloud of points using as few principal components as possible, while still ensuring that a large percentage of the cloud is described. This percentage can be varied depending on the analyst's needs.

PCA modeling has been more completely described by G. H. Golub and C. F. Van Loan in *Matrix Computations*, John Hopkins University Press, 1983, and by J. E. Jackson in *Journal of quality Technology*, 1980, vol. 12. pg 201. These articles are hereby incorporated by reference. These references disclose that in a given matrix X, consisting of m rows of samples, and n columns of wavelengths, so that each point in the matrix is filled with an absorbance reading of the indicated sample at the indicated wavelength, the PCA model is described by the following equations:

$$X = USV'$$

where U is an mxr matrix of eigenvectors for the matrix XX'; S is an rxr diagonal matrix containing singular values; V' is an rxn matrix of eigenvectors for the matrix X'X; and r is the rank of the matrix X. V is an orthonormal matrix (i.e. V'V=I), therefore this equation can be rearranged as follows:

$$XV = US$$

The eigenvectors in V describe the orientation of the principal component hyperplane in the wavelength space that contains the calibration samples. The product of the matrices U and S forms a matrix called the score matrix. This matrix contains the projections of the spectra on the new coordinate system defined by the eigenvectors. The rank, r, defines the dimensionality of the space required to contain all of the points in the space. For the purposes of this invention, the number of eigenvectors and the dimensionality of the PCA model will always be less than the full rank of X. This means that there will always be a finite residual spectrum that was not described by the PCA model. These residual spectra can be obtained using the following formula:

$$\text{Resid} = X(I - V_k V_k')$$

where Resid is an mxn matrix of residual spectra; X is the mxn matrix of original spectra; I is an nxn identity matrix; and $V_k$ is an nxk matrix containing the first k columns of V (where k is less than r and k defines the dimensionality of the PCA model).

To use the residuals to identify outliers, a system was developed to characterize the calibration residual spectra. As previously discussed, it should be understood that the present description uses "spectrum" for ease of discussion only and that any set of multivariate data capable of being measured is amenable to the technique.

The first step is to calculate the average calibration residual spectrum, which is the spectrum formed by averaging the absorption values at each wavelength for all calibration residual spectra. The Euclidian distance of each calibration residual spectrum from the average calibration residual spectrum was then calculated. Any sample having a residual (calculated as described above) whose Euclidean distance from the average residual is statistically different from the group of Euclidean distances obtained for the calibration set can be labeled an outlier. "Statistically different" as used herein includes any situation where a sample (or a series of samples) produces a Euclidean distance which would not be expected given the variances observed in the calibration set. Although several methods are known for making the determination of whether a single value (or a trend consecutive values) is statistically different from a group of values, the following method is preferred. This method is presented for exemplary purposes only, however, and should not be viewed as limiting the invention to this particular method.

First, the average of the distance between the residual for each calibration set member and the average calibration residual is calculated. Next the standard deviation for these distances is obtained. Once the average and standard deviation are known for the calibration set, a value herein termed the "t-distance" can be calculated for each member of the calibration set according to the following formula:

$$t\text{-}distance_i = \frac{DIS_i - AVE}{STD}$$

where $DIS_i$ is the distance of the ith residual spectrum from the average residual spectrum; and AVE and STD are the average and the standard deviation of the distances of the calibration set members from the average residual spectrum. In this way, a residual spectrum is characterized by a single value and control chart techniques can be used to classify a spectrum as an outlier.

With enough principal components in the PCA model, all of the variation in the calibration set could be exactly described. A model which exactly described the calibration set would not help determine whether a new spectrum is an outlier, however, as if the new spectrum had a noise structure different from the calibration set then it would be labelled an outlier, regardless of other similarities. To determine the number of principal components to include thereby ensuring that the PCA model contains few enough principal components to allow flexibility, a leave-one-out cross-validation technique can be used. This process operates by removing one of the members of the calibration set, recalculating the model, and then treating the removed calibration set member as an unknown. If this results in a t-distance greater than preselected value (e.g three if the t-distances are assumed to be approximately normally distributed), then either the spectrum was incorrectly chosen as a calibration set member or the model is too precise and a principal component should be removed. This process is repeated for each of the members of the calibration set until all of them produce t-distances of less than the preselected value when they are "left-out" of the calibration set and treated as an unknown.

Once the model has been shown to accurately represent the calibration spectra while allowing enough flexibility, then unknown samples can be evaluated. The procedure is similar to the treatment of the calibration spectra. First, the spectrum is represented by a point in the multidimensional space. Then the point is projected onto the model and a residual spectrum is obtained. Next the Euclidian distance between the residual spectrum for the sample and the average residual from the calibration set is measured, and a t-distance calculated. Any unknown sample whose residual spectrum has a t-distance greater than the preselected value or is otherwise deemed abnormal using other control chart criteria would be considered an outlier, and the operator would be promptly notified.

This system was tested using data gathered from a gas chromatograph. It was soon discovered that in gas chromatography certain elements change over a period of time.

Thus, new models had to be constructed frequently to take into account the changing circumstances. As this is very inconvenient as well as wasteful, an alternative was sought.

It was discovered that the chromatograms could be broken up into separate sub-parts (sub-chromatograms), and that each of these sub-chromatograms could be individually modeled using a technique such as PCA. A chromatogram can be thought of as a function of time F(t), which can be written as the sum of a series of separate functions containing unique information. For example, a chromatogram can be represented as the sum of the baseline offset, the baseline shape, the peak information, and the typically higher frequency noise. Evaluating each of these sub-chromatograms separately results in a more sensitive analysis, and the analyst can see which component of the chromatogram is abnormal. Accordingly, if the baseline shape changes over time, the analyst will be made aware of the change, but will know that valid peak information is still being generated.

Figure 1:
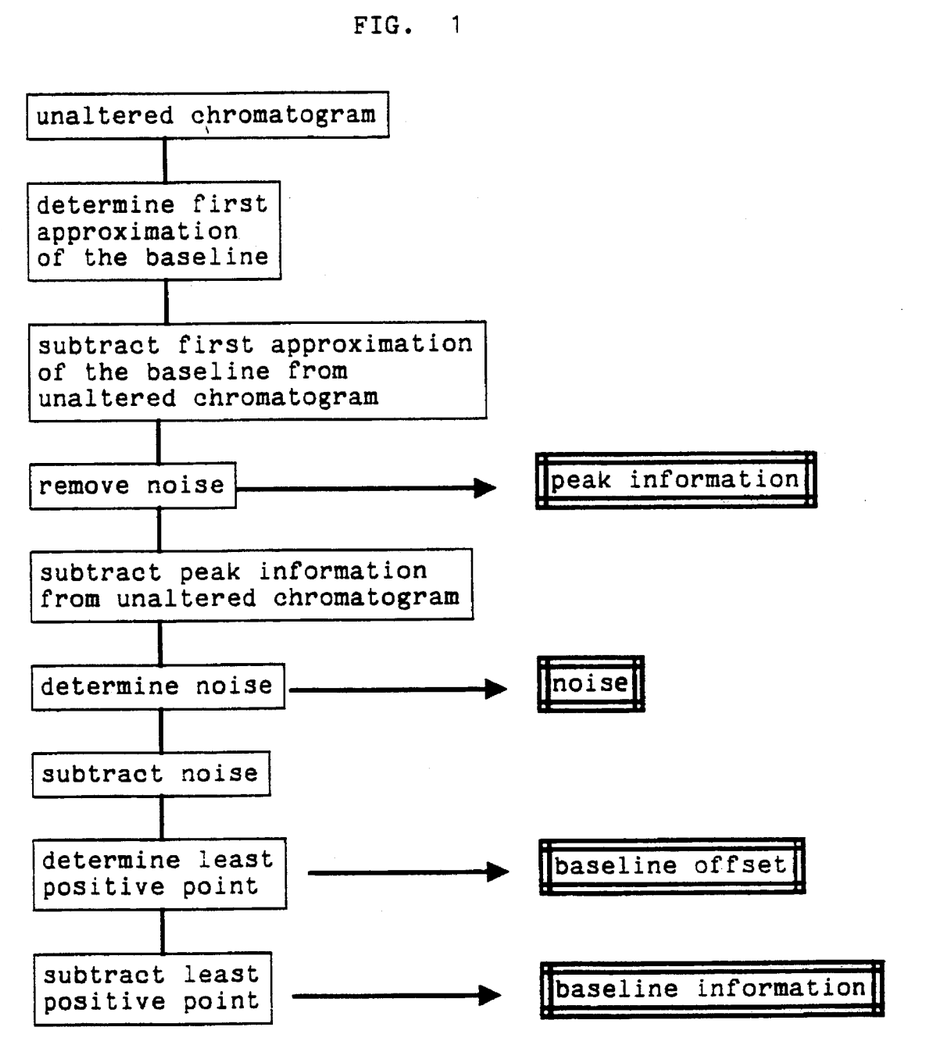
FIG. 1 is a flow chart of a preferred embodiment of the method for separating a set of multivariate data into sub-parts, illustrating how a chromatogram can be broken up into the sub-chromatograms of peak information, baseline shape, baseline offset, and noise.

A method was developed to separate out the various sub-parts from a set of multivariate data. This allows for a more sensitive analysis, and the identification of the source of the variation. As seen in the flowchart of FIG. 1, this method comprises first identifying the portions of the multivariate data which contain peak information. The portions so identified are then subtracted from the set of multivariate data. These removed portions are then replaced using linear interpolation or some other method to approximate what the baseline would have been without the peaks. Finally, this approximation of the baseline is subtracted from the unaltered set of multivariate data, thereby forming a set of data containing peak information.

The peak information can be subtracted from the unaltered set of multivariate data to form a set of data containing baseline shape. Noise and the baseline offset can be removed from this set of data to provide greater separation. Thus, it is possible to separate a set of multivariate data into peak information, baseline shape, baseline offset and noise. Furthermore these can be combined in any way depending on the needs of a particular analysis.

Figure 2:
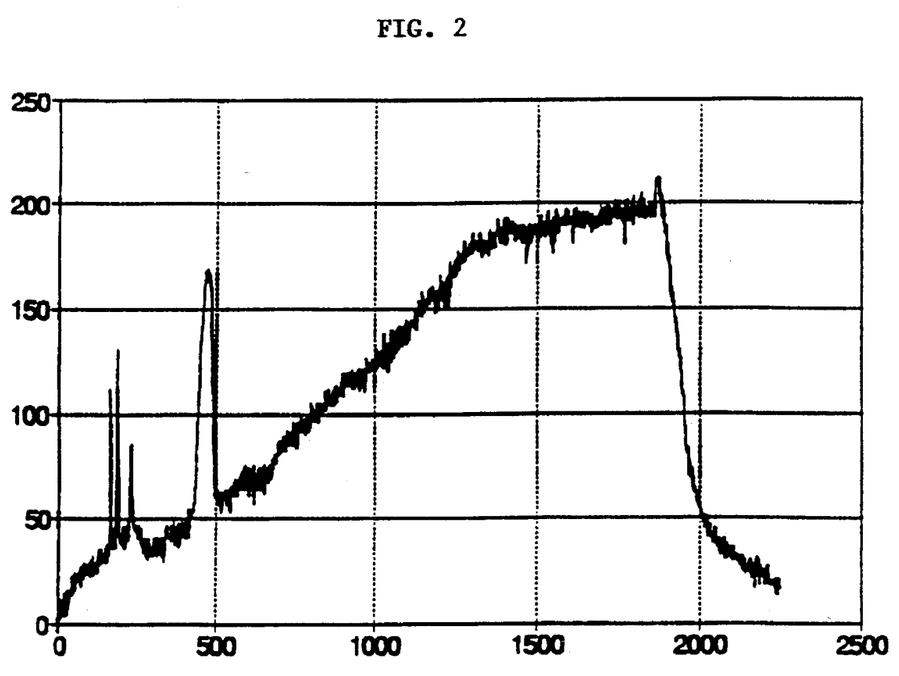
FIG. 2 is a copy of an unaltered chromatogram used to demonstrate how such a chromatogram can be broken up into separate sub-chromatograms.

A preferred embodiment of accomplishing the method for a chromatogram is set out in the following paragraphs for exemplary purposes. It should be understood, however, that the following is only one way of accomplishing the method and that each individual step may be accomplished by other equivalent methods known in the art (e.g. a cubic spline fit can be used to obtain the second derivative, or smoothing techniques can be used to remove the noise). Furthermore, the preferred embodiment described below contains specific parameters for exemplary purposes only. These parameters were used to adequately separate the chromatogram shown in FIG. 2 into sub-chromatograms as seen in FIGS. 3–6. Practitioners in the art will understand that these parameters can be varied to suit the needs of the individual analysis.

First, the second derivative of the chromatogram was calculated. The second derivative was obtained using the Savitsky-Golay method (Abraham Savitsky, Marcel Golay, *Analytical Chemistry*, 36, No. 8, pg. 1627 July, 1964), with a moving window for the second derivative containing 31 points (parameter 1). Next, it was determined that the first fifty points (parameter 2) contained no peak information and that this region was typical of the noise and baseline offset seen in the whole chromatogram. The average and standard deviation of the values of the points in this region were then calculated. The entire second derivative was then examined and any point which had a value greater than three standard deviations (parameter 3) away from the average value of the first fifty points was assumed to contain peak information.

Furthermore, to be sure that the rising and falling edges of the peaks, as well as the points of inflection, were not considered baseline points, the ten points (parameter 4) before and after each point identified as a peak were also defined to be part of that peak.

Figure 3:
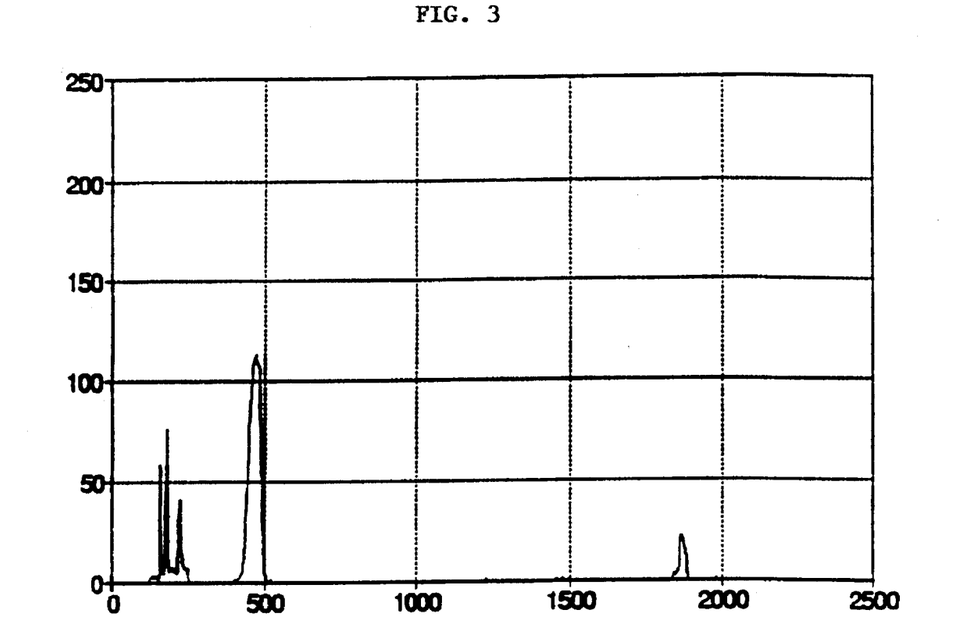
FIG. 3 is the peak information sub-chromatogram, which has been separated from the unaltered chromatogram in FIG. 2 according to the present invention.

Once the location of the peaks had been determined, the peaks were removed from the original chromatogram leaving blank regions. These regions were filled in using a linear interpolation of the points which framed the region. This resulted in a first approximation of the baseline. This first approximation of the baseline was then subtracted from the original chromatogram leaving only peak information. The peak information was then smoothed using a Savitsky-Golay smooth with a moving window of 11 points (parameter 5). This resulted in the peak sub-chromatogram (FIG. 3).

Figure 4:
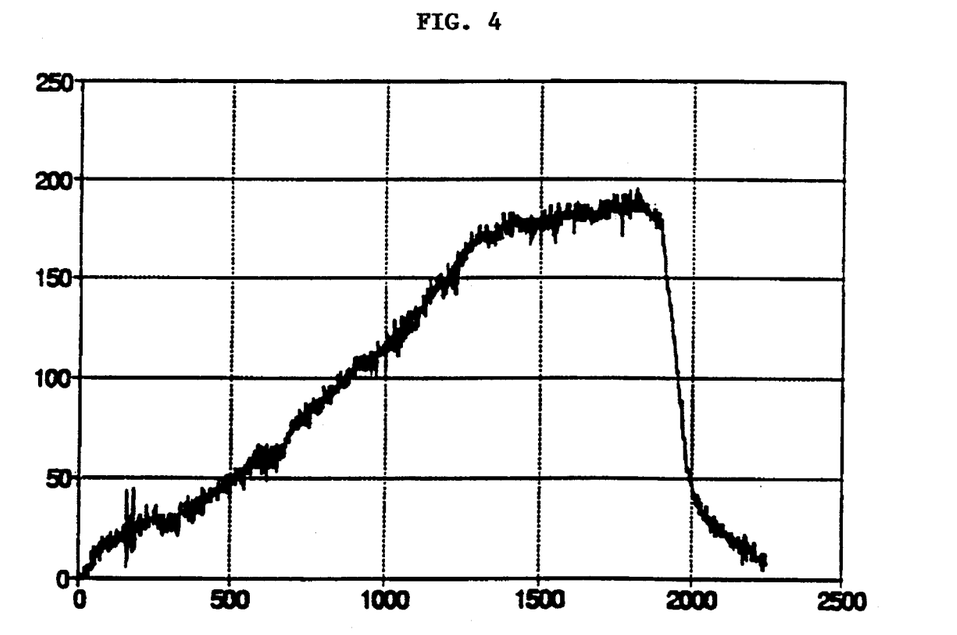
FIG. 4 shows the chromatogram remaining after removing the peak information shown in FIG. 3 from the unaltered chromatogram of FIG. 2, so that the noise and baseline shape may be determined.
Figure 5:
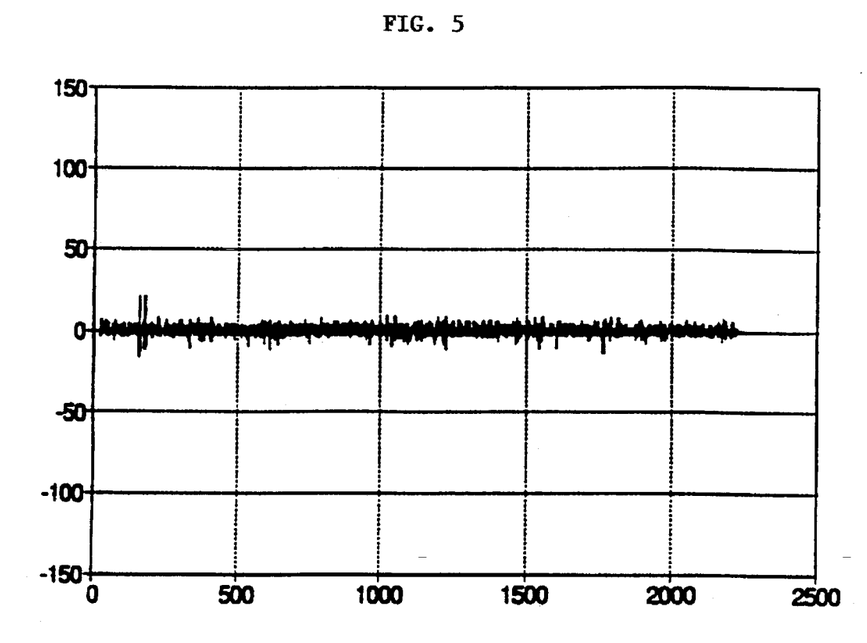
FIG. 5 is the noise obtained from the chromatogram in FIG. 4, separated according to the present invention.
Figure 6:
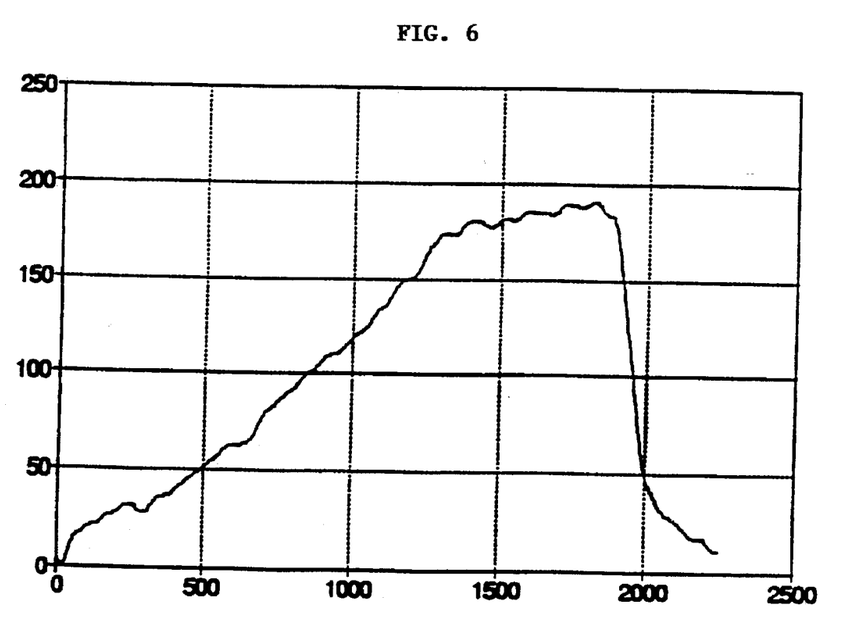
FIG. 6 is the baseline information obtained by removing the noise and baseline offset from the chromatogram in FIG. 4.

The peak sub-chromatogram was then subtracted from the original chromatogram. This left a sub-chromatogram (hereinafter referred to as sub-chromatogram A) containing the baseline shape, the baseline offset and noise (FIG. 4). Sub-chromatogram A was then subjected to a Fourier transformation, and the resultant interferogram was subjected to a boxcar filter. The boxcar filter used zeros for all Fourier coefficients above coefficient 101 (parameter 6). After filtering, an inverse Fourier transformation was performed. This resulted in a sub-chromatogram (sub-chromatogram B) which contained only the baseline shape and baseline offset. Sub-chromatogram B was subtracted from sub-chromatogram A yielding the noise sub-chromatogram (FIG. 5). The least positive point in sub-chromatogram B was defined as the baseline offset and was subtracted from sub-chromatogram B yielding the baseline shape sub-chromatogram (FIG. 6).

Any combination of the three sub-chromatograms (peak, noise and baseline shape) and the offset can be used to form a new sub-chromatogram if the separation into four parts is not appropriate.

Any resulting sub-chromatogram containing baseline shape and/or peak information can be evaluated using the PCA modeling method previously discussed. The offset value by itself is not multivariate and is therefore not amenable to PCA modeling. Standard control chart techniques can be used to monitor the offset. Similarly, a sub-chromatogram containing only noise or noise with the baseline offset should contain only random variation and consequently is not suited to PCA modeling. Control chart techniques can be used to monitor various statistics (e.g. maximum value, minimum value, standard deviation, sum of absolute values, and mean value) of these sub-chromatograms in order to detect outliers.

Accordingly, a spectrum or chromatogram can be broken up into sub-parts such as peak information, noise, baseline offset, and baseline shape. Each of the sub-parts can be monitored to see if it is within the normal range expected for the analysis. In this way the observer can tell which type of feature in the multivariate data is abnormal. Furthermore, dividing up the multivariate data makes the analysis more sensitive. For example, in chromatography if the baseline offset drifts from run to run, then the cloud of points in the multidimensional space will necessarily be more spread out, reflecting the fact that identical samples could have different responses at a particular time after sample injection depending on the baseline offset. Spreading out the cloud of points may hide some slight variation which has occurred in some other feature in the chromatogram for which little variation is expected. Consequently, separating the data into various sub-chromatograms allows the system to confidently classify as outliers, samples with slight variations in a sub-chromatogram for which there should be little or no variation.

This technique can be placed on-line in a chemical process, furthering the automation of such processes. A computing device can be programmed to make the necessary calculations described above. This computing device can then evaluate the chromatograms or spectra which are routinely generated for samples of chemical processes. When an outlier is detected, the computing means can signal an operator and/or shut down the process, so that no resources are wasted producing material which does not meet the required specifications.

It will be appreciated that the above disclosed embodiments are suited to achieve the aforementioned objectives of the present invention. In addition, it is evident that those skilled in the art, once given the benefit of the foregoing disclosure, may make modifications of the specific embodiments described above without departing from the spirit of the invention. Such modifications are to be considered within the scope of the present invention which is limited solely by the scope and spirit of the appended claims.

What is claimed is:

1. A method of using a computing device to conduct an analysis of a sample, comprising:

(a) performing an analytical technique on the sample, said analytical technique being selected from the group consisting of chromatography and spectrometry so that a set of multivariate data which corresponds to the sample is produced;

(b) obtaining a series of representative multivariate data sets, wherein the representative multivariate data sets are obtained from the same type of analysis as was performed to produce the set of multivariate data in step (a);

(c) creating a model of the series of multivariate data sets obtained in step (b);

(d) creating individual residuals describing the portion of the multivariate data set obtained for each member of the calibration set which is not described by the model created in step (c);

(e) creating an average residual by averaging the individual residuals created in step (d);

(f) determining the distance between the individual residual for each member of the calibration set and the average residual;

(g) creating a residual describing the portion of the multivariate data set produced in step (a) which is not described by the model created in step (c);

(h) determining the distance between a residual obtained in step (g) and the average residual created in step (e);

(i) labeling as an outlier any set of multivariate data whose distance obtained in step (h) is statistically different from the set of distances determined in step (f); and (j) checking for changes in feedstock, chemical processes and/or instruments used to make or evaluate the sample whenever one or more sets of multivariate data has been labelled as an outlier.

2. The method of claim 1 wherein the procedure used to create the model of the calibration set is Principal Component Analysis.

3. The method of claim 1 wherein the multivariate data is separated into a plurality of sub-parts prior to creating a model so that an outlier in one or more selected sub-parts can be detected.

4. The method of claim 3 wherein at least one of the sub-parts includes a member of the group consisting of peak information, baseline shape, baseline offset and noise.

5. The method of claim 4 wherein one of the sub-parts includes peak information, separated by a method which comprises the following steps:

(a) obtaining a set of multivariate data which includes peak information;

(b) identifying the portions of the multivariate data which contain peak information;

(c) subtracting the portions identified in step (b) from the set of multivariate data obtained in step (a);

(d) replacing the points subtracted in step (c) from the set of multivariate data obtained in step (a), so that a first approximation of the baseline is formed; and (e) subtracting the first approximation of the baseline formed in step (d) from the set of multivariate data obtained in step (a), thereby forming a set of data containing peak information.

6. The method of claim 5 wherein step (e) further comprises smoothing out the peak information data.

7. The method of claim 6 wherein a second sub-part includes baseline shape, separated by a method which comprises:

(f) subtracting the set of data formed in step (e) from the set of multivariate data obtained in step (a), thereby forming a set of data containing baseline shape.

8. The method of claim 7 wherein a third sub-part includes noise separated by a method which comprises:

(g) subjecting the set of data formed in step (f) to a Fourier transformation and then a filtering operation; and (h) subtracting the set of data formed in step (g) from the set of data formed in step (f) thereby forming a set of data containing noise information.

9. The method of claim 8 wherein a fourth sub-part includes the baseline offset which is defined as being the least positive point in the set of multivariate data obtained in step (a).

10. The method of claim 7 wherein step (f) further comprises:

defining the baseline offset to be the least positive point in the set of data formed in step (d);

subtracting the baseline offset from the set of data containing baseline shape; and subjecting the resulting set of data to a Fourier transformation and then a filtering operation.

11. The method of claim 5 wherein step (b) comprises:

calculating the values for the second derivative of the set of multivariate data obtained in step (a);

selecting a region in the set of multivariate data which is known not to contain peaks;

averaging the values for the second derivative of the points in the region;

calculating a standard deviation for the values for the second derivative of the points in the region; and defining any point whose second derivative is further than a preselected number of standard deviations from the average value for the second derivative in the region to be part of a peak.

12. The method of claim 11 further comprising defining any point within a preselected number of points from a point defined as a peak in claim 9 to be part of a peak.

13. The method of claim 5 wherein step (d) includes using linear interpolation to replace the points subtracted in step (c).

14. A method of using a computing device to examine multivariate data to determine outliers, comprising the steps of:

11

(a) selecting a calibration set of multivariate data;

(b) representing each member of the calibration set as a single point in a multidimensional axes system;

(c) constructing a model describing the points of step (b);

(d) obtaining a residual for each member of the calibration set by calculating the portion of each member which is not depicted by the model constructed in step (c);

(e) creating an average residual by averaging the residuals of all of the calibration set members;

(f) determining the distance between each of the residuals obtained in step (d) and the average residual obtained in step (e);

(g) determining the average and standard deviation of the distances obtained in step (f);

(h) calculating a t-distance for each member of the calibration set according to the formula:

$$t\text{-}distance = \frac{DIS_i - AVE}{STD}$$

where $Dis_i$ is the distance obtained in step (f) for any member i, and AVE and STD are the average and standard deviation values obtained in step (g);

(i) acquiring a set of multivariate data from a sample;

(j) obtaining a residual for the sample by calculating the portion of the sample which was not depicted by the model constructed in step (c);

(k) determining the distance between the residual obtained in step (j) and the average residual obtained in step (e);

(l) calculating a t-distance for the sample according to the formula:

$$t\text{-}distance = \frac{DIS_{sam} - AVE}{STD}$$

where $Dis_{sam}$ is the distance obtained in step (k), and AVE and STD are the average and standard deviation values obtained in step (g); and (m) labeling as an outlier any sample whose t-distance is statistically different from the t distances obtained in step (h).

(n) checking for changes in feedstock, chemical processes and/or instruments used to make or evaluate the sample whenever a sample has been labelled as an outlier.

15. The method of claim 14 wherein principal Component Analysis is used to construct the model in step (c).

16. A method of using a computing device to separate a set of multivariate data into a plurality of sub-parts, wherein each sub-part comprises at least one member selected from the group consisting of peak information, baseline shape, baseline offset, and noise comprising the steps of:

(a) performing an analysis on a sample to obtain a set of multivariate data which includes peak information;

(b) calculating the values for the second derivative of the set of multivariate data obtained in step (a);

(c) selecting a region in the set of multivariate data which is known to contain substantially no peak information;

(d) averaging the values for the second derivative of the points in the region;

(e) calculating a standard deviation for the values for the second derivative of the points in the region; and (f) defining any point whose second derivative is further than a preselected number of standard deviations from the average value for the second derivative in the region to be part of a peak;

(g) removing the portions identified in step (f) from the set of multivariate data obtained in step (a);

(h) replacing the points removed in step (g) from the set of multivariate data obtained in step (a), so that a first approximation of the baseline is formed; and (i) subtracting the first approximation of the baseline formed in step (h) from the set of multivariate data obtained in step (a), thereby forming a set of data comprising peak information.

17. The method of claim 16 wherein step (h) includes using linear interpolation to replace the points subtracted in step (g).

18. The method of claim 16 further comprising:

(j) smoothing out the set of data formed in step (i).

19. The method of claim 18 further comprising:

(k) subtracting the set of data formed in step (j) from the set of multivariate data obtained in step (a), thereby forming a set of data comprising baseline shape, noise and baseline offset.

20. The method of claim 19 further comprising:

(l) subjecting the set of data formed in step (k) to a Fourier transformation and then a filtering operation; and (m) subtracting the set of data formed in step (l) from the set of data formed in step (k) thereby forming a set of data comprising noise.

21. The method of claim 20 further comprising:

(n) defining the baseline offset to be the least positive point in the set of multivariate data obtained in step (a).

22. The method of claim 21 further comprising:

(o) subtracting the baseline offset defined in step (n), and the set of data formed in step (m) from the set of data obtained in step (k).

23. The method of claim 16 further comprising defining any point within a preselected number of points from a point defined as a peak in claim 16 to be part of a peak.

24. In a method of conducting an analysis of a sample wherein a set of multivariate data characteristic of the sample is produced through physical manipulations of the sample, and this set of multivariate data is compared to multivariate data obtained from samples having known properties which were similarly manipulated, the improvement comprising: using a computing device to rapidly identify when problems exist in either the sample or the instrumentation by determining whether the set of multivariate data produced for the sample is within an expected range; wherein the determination of whether the set of multivariate data produced for the sample is within an expected range is made by (a) obtaining a series of representative multivariate data sets;

(b) creating a model of the series of multivariate data sets obtained in step (a);

(c) creating individual residuals describing the portion of the multivariate data set obtained for each member of the calibration set which is not described by the model created in step (b);

(d) creating an average residual by averaging the individual residuals created in step (c);

(e) determining the distance between the individual residual for each member of the calibration set and the average residual;

(f) performing the same type of physical manipulations as was performed to create the series of multivariate data sets obtained in step (a) on a sample, thereby obtaining an additional multivariate data set;

(g) creating a residual describing the portion of the multivariate data set obtained in step (f) which is not described by the model created in step (b);

(h) determining the distance between a residual obtained in step (g) and the average residual created in step (d);

(i) labeling as an outlier any set of multivariate data whose distance obtained in step (h) is statistically different from the set of distances determined in step (e).

25. A method of conducting an analysis of a sample comprising:

(A) physically manipulating the sample so that a set of multivariate data characteristic of the sample is produced;

(B) using a computing device to determine whether the set of data produced in step (A) is an outlier;

(C) if the set of data produced in step (A) is not an outlier, then estimating the properties of the sample by comparing the set of multivariate data produced in step (A) with multivariate data obtained under similar circumstances for samples having known properties;

(D) if the set of data produced in step (A) is an outlier, then checking for changes in feedstock, chemical processes and/or instrumentation used to make or evaluate the sample;

wherein step (B) is accomplished by (a) obtaining a series of representative multivariate data sets;

(b) creating a model of the series of multivariate data sets obtained in step (a);

(c) creating individual residuals describing the portion of the multivariate data set obtained for each member of the calibration set which is not described by the model created in step (b);

(d) creating an average residual by averaging the individual residuals created in step (c);

(e) determining the distance between the individual residual for each member of the calibration set and the average residual;

(f) creating a residual describing the portion of the multivariate data set obtained in step (A) which is not described by the model created in step (b);

(g) determining the distance between a residual obtained in step (f) and the average residual created in step (d);

(h) labeling as an outlier any set of multivariate data whose distance obtained in step (g) is statistically different from the set of distances determined in step (e).

26. In a method of carrying out a chemical reaction wherein feedstocks are reacted under conditions sufficient to produce reaction products and wherein the reaction products are sampled and wherein a set of multivariate data describing the sample is produced, and the set of multivariate data is analyzed to ensure that the reaction products are within a desired range, the improvement comprising: automatically determining when the analysis is an outlier and checking for changes in the feedstock, reaction conditions, and/or the instrumentation used to perform the analysis whenever an outlier is determined; wherein the automatic determination is accomplished by (a) obtaining a series of multivariate data sets representative of range of samples expected to be obtained;

(b) creating a model of the series of multivariate data sets obtained in step (a);

(c) creating individual residuals describing the portion of the multivariate data set obtained for each member of the calibration set which is not described by the model created in step (b);

(d) creating an average residual by averaging the individual residuals created in step (c);

(e) determining the distance between the individual residual for each member of the calibration set and the average residual;

(f) creating a residual describing the portion of the multivariate data set obtained in step (A) which is not described by the model created in step (b);

(g) determining the distance between a residual obtained in step (f) and the average residual created in step (d);

(h) labeling as an outlier any set of multivariate data whose distance obtained in step (g) is statistically different from the set of distances determined in step (e).

* * * * *